(12) United States Patent
Fraser et al.

(10) Patent No.: US 7,960,705 B2
(45) Date of Patent: Jun. 14, 2011

(54) EXCIMER RADIATION LAMP ASSEMBLY, AND SOURCE MODULE AND FLUID TREATMENT SYSTEM CONTAINING SAME

(75) Inventors: Jim Fraser, St. Thomas (CA); Michael Sasges, Victoria (CA)

(73) Assignee: Trojan Technologies, London, Ontario (CA)

( * ) Notice: Subject to any disclaimer, the term of this patent is extended or adjusted under 35 U.S.C. 154(b) by 103 days.

(21) Appl. No.: 12/158,849

(22) PCT Filed: Dec. 21, 2006

(86) PCT No.: PCT/CA2006/002085
§ 371 (c)(1), (2), (4) Date: Dec. 15, 2008

(87) PCT Pub. No.: WO2007/071043
PCT Pub. Date: Jun. 28, 2007

(65) Prior Publication Data
US 2009/0101835 A1    Apr. 23, 2009

Related U.S. Application Data

(60) Provisional application No. 60/752,025, filed on Dec. 21, 2005.

(51) Int. Cl.
*G01N 23/12* (2006.01)
(52) U.S. Cl. .................. 250/436; 250/455.11

(58) Field of Classification Search .................. 250/436, 250/435, 504 R, 455.11; 422/186.3, 186.07, 422/186; 315/248, 246; 313/621, 634
See application file for complete search history.

(56) References Cited

U.S. PATENT DOCUMENTS

| | | | |
|---|---|---|---|
| 3,935,491 A * | 1/1976 | Hugot | 313/25 |
| 4,837,484 A | 6/1989 | Eliasson et al. | |
| 5,194,740 A | 3/1993 | Kogelschatz et al. | |
| 5,386,170 A | 1/1995 | Kogelschatz | |
| 5,471,063 A | 11/1995 | Hayes et al. | |
| 5,757,132 A | 5/1998 | Matsuno et al. | |
| 6,193,939 B1 * | 2/2001 | Kozlowski | 422/186.3 |
| 6,201,355 B1 | 3/2001 | Morgan et al. | |
| 7,615,160 B2 * | 11/2009 | Collins et al. | 210/748.11 |

OTHER PUBLICATIONS

International Search Report for International Application No. PCT/CA2006/002085; 2006.

* cited by examiner

*Primary Examiner* — Kiet T Nguyen
(74) *Attorney, Agent, or Firm* — Katten Muchin Rosenman, LLP

(57) ABSTRACT

There is described an excimer radiation lamp assembly. The lamp assembly comprises: an elongate member having an annular cross-section to define an elongate passageway aligned with a longitudinal axis of the lamp assembly; an electrode element in electrical connection with at least a portion of the elongate passageway; and a cooling element disposed in the elongate passageway, the cooling element being electrically isolated with respect to the electrode element.

19 Claims, 9 Drawing Sheets

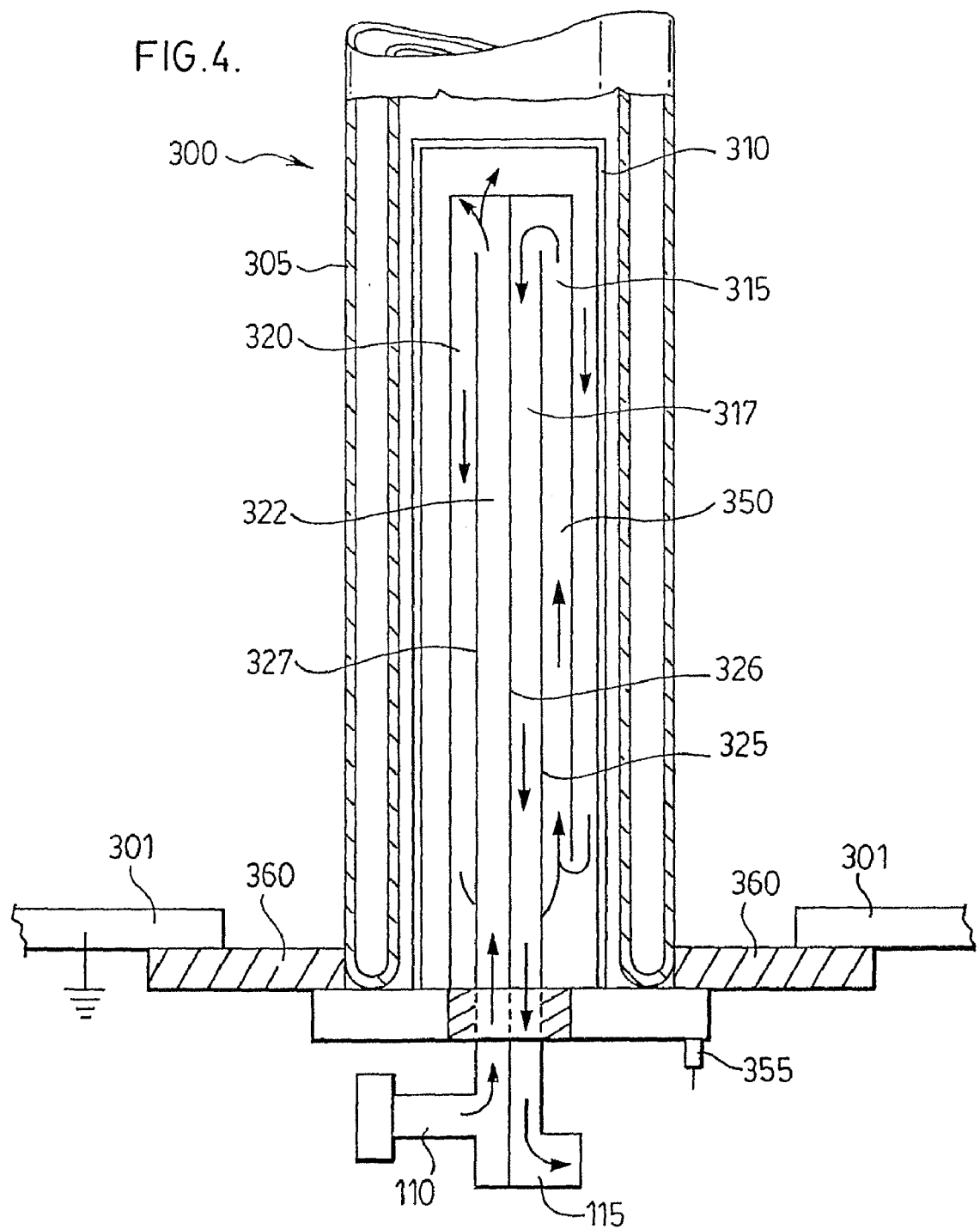

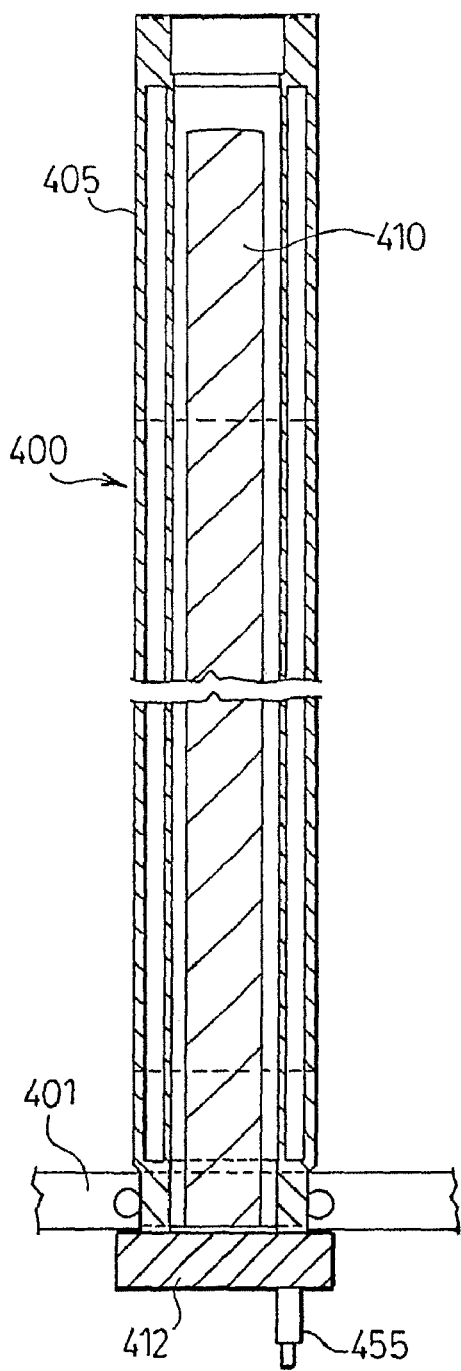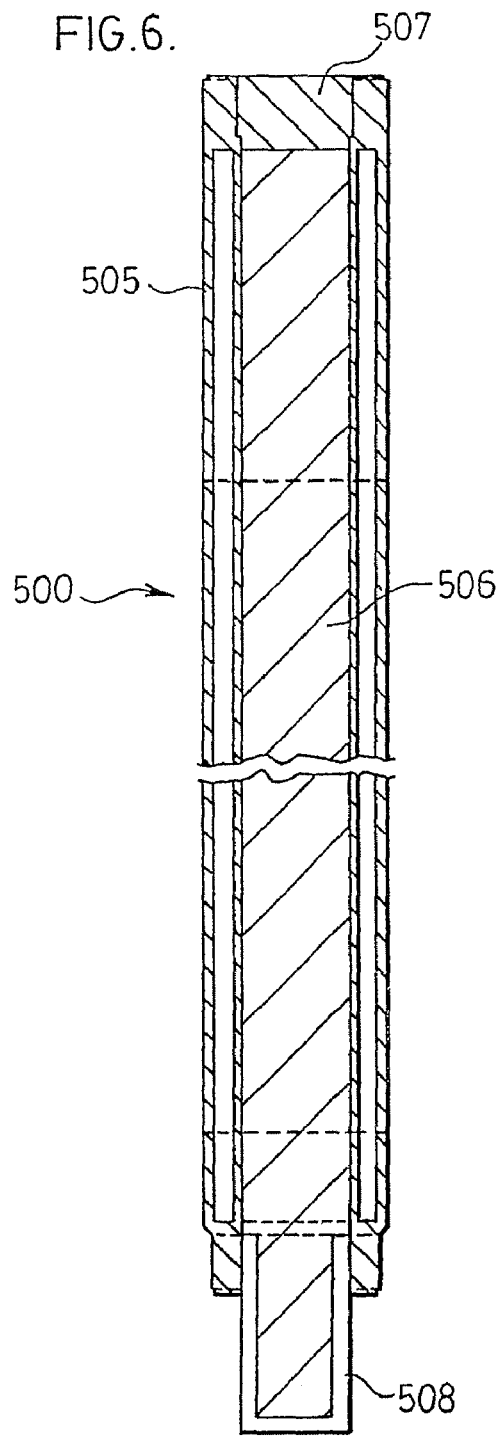

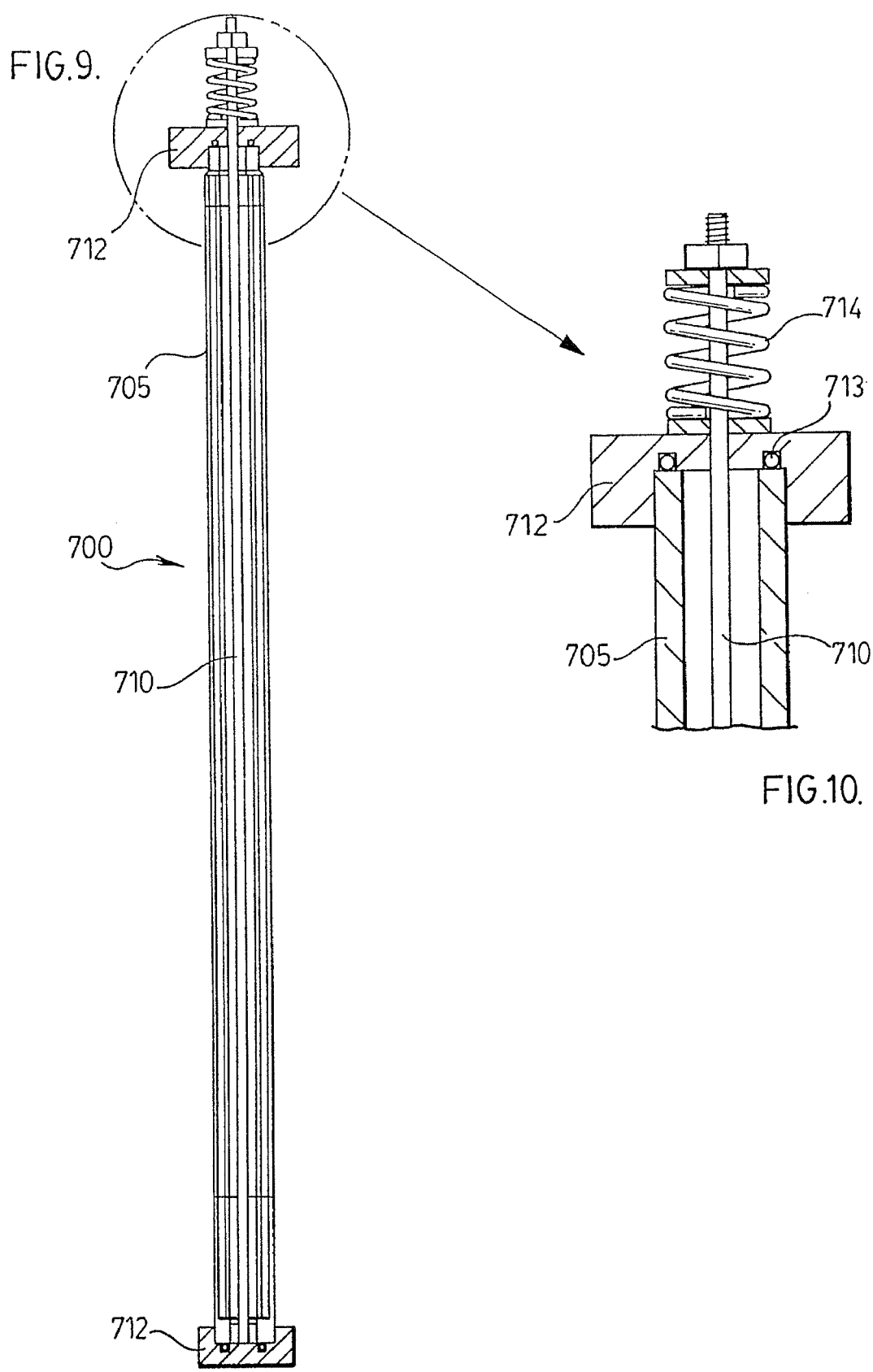

EXCIMER RADIATION LAMP ASSEMBLY, AND SOURCE MODULE AND FLUID TREATMENT SYSTEM CONTAINING SAME

FIELD OF THE INVENTION

In one of its aspects, the present invention relates to an excimer radiation lamp assembly. In another of its aspects, the present invention relates to a radiation source module comprising the excimer radiation lamp assembly. In another of its aspects, the present invention relates to a fluid treatment system comprising the excimer radiation lamp assembly.

DESCRIPTION OF THE PRIOR ART

Fluid treatment systems are known generally in the art.

For example, U.S. Pat. Nos. 4,482,809, 4,872,980, 5,006,244, 5,418,370, 5,539,210 and Re:36,896 (all in the name of Maarschalkerweerd and all assigned to the assignee of the present invention) all describe gravity fed fluid treatment systems which employ ultraviolet (UV) radiation.

Generally, such prior fluid treatment systems employ an ultraviolet radiation lamp to emit radiation of a particular wavelength or range of wavelengths (usually between 185 and 400 nm) to effect bacterial kill or other treatment of the fluid being treated. Many conventional ultraviolet radiation lamps are known as "low pressure" mercury lamps.

In recent years, the art in low pressure mercury lamps has evolved with the development of the so-called Low Pressure, High Output (LPHO) and amalgam UV radiation lamps. These lamps have found widespread use in UV radiation water treatment systems, particularly those used for treatment of municipal drinking water and wastewater. As used herein, the term "low pressure" UV radiation lamp is intended to encompass conventional UV radiation lamps, LPHO UV radiation lamps and amalgam UV radiation lamps.

Low pressure UV radiation lamps and medium pressure UV radiation lamps are the current standard used for UV radiation treatment of municipal drinking water and wastewater.

In recent years, there has been development in the area of so-called excimer radiation lamps. These lamps have the potential to be used in a variety of applications. One such application is UV radiation treatment of water—e.g., municipal drinking water and wastewater.

To date, there has been little or no development of excimer radiation lamps for use in the UV radiation treatment of water—e.g., municipal drinking water and wastewater. Further, it is known that excimer radiation lamps require cooling for optimal operation.

Accordingly, there is a real need in the art for an excimer radiation lamp that is well suited for use in the UV radiation treatment of water—e.g., municipal drinking water and wastewater. More particularly, there is a real need in the art for an excimer radiation lamp that is well suited for use in the UV radiation treatment of water on the one hand and incorporates the required cooling function on the other hand.

In a similar vein, there is a need in the art for a radiation source module and a fluid treatment system incorporating such an excimer radiation lamp.

SUMMARY OF THE INVENTION

It is an object of the present invention to provide a novel excimer radiation lamp assembly.

It is a further object of the invention to provide a novel radiation source module.

It is yet a further object of the present invention to provide a novel fluid treatment system.

Accordingly, in one of its aspects, the present invention provides an excimer radiation lamp assembly comprising:

an elongate member having an annular cross-section to define an elongate passageway aligned with a longitudinal axis of the lamp assembly;

an electrode element in electrical connection with at least a portion of the elongate passageway; and a cooling element disposed in the elongate passageway, the cooling element being electrically isolated with respect to the electrode element.

In another of its aspects, the present invention provides an excimer radiation lamp assembly comprising:

an elongate member having an annular cross-section to define an elongate passageway aligned with a longitudinal axis of the lamp assembly;

an electrode element in electrical connection with at least a portion of the elongate passageway; and a cooling circuit disposed in the elongate passageway and configured to receive a coolant, the cooling circuit having: (i) a coolant inlet, (ii) a coolant outlet and (iii) a length such that an applied voltage at the electrical connection is reduced by a factor of at least 0.10 at the coolant inlet.

In another of its aspects, the present invention provides an excimer radiation lamp assembly comprising:

an elongate member having an annular cross-section to define an elongate passageway aligned with a longitudinal axis of the lamp assembly;

an electrode element in electrical connection with at least a portion of the elongate passageway; and a cooling circuit disposed in the elongate passageway and configured to receive a coolant, the cooling circuit having: (i) a coolant inlet, (ii) a coolant outlet and (iii) a cooling loop configured to be in heat exchange contact with fluid from a fluid treatment system in which the radiation assembly is disposed.

In another of its aspects, the present invention provides an excimer radiation lamp assembly comprising:

an elongate member having an annular cross-section to define an elongate passageway aligned with a longitudinal axis of the lamp assembly;

an electrode element in electrical connection with at least a portion of the elongate passageway; and a cooling circuit disposed in the elongate passageway and configured to receive a coolant, the cooling circuit having: (i) a coolant inlet in fluid communication with fluid from a fluid treatment system in which the radiation assembly is disposed, (ii) a coolant outlet in fluid communication with fluid from a fluid treatment system in which the radiation assembly is disposed and (iii) motive means to cycle the coolant from the cooling circuit to the fluid treatment system.

In another of its aspects, the present invention provides an excimer radiation lamp assembly comprising:

an elongate member having an annular cross-section to define an elongate passageway aligned with a longitudinal axis of the lamp assembly;

an elongate electrode element disposed in the elongate passageway to define an annular passageway configured to receive an electrically conductive fluid; and a cooling element disposed in the elongate electrode, the cooling element comprising a substantially electrically non-conductive heat transfer element configured to convey heat from the elongate electrode.

In another of its aspects, the present invention provides an excimer radiation lamp assembly comprising:

an elongate member having an annular cross-section to define an elongate passageway aligned with a longitudinal axis of the lamp assembly;

an electrode element in electrical connection with at least a portion of the elongate passageway; and the elongate passageway comprising a heat pipe element, the heat pipe element configured to transfer heat from the electrode element.

In another of its aspects, the present invention provides an excimer radiation lamp assembly comprising:

an elongate member having an annular cross-section to define an elongate passageway aligned with a longitudinal axis of the lamp assembly;

an elongate electrode element disposed in the elongate passageway to define a gap therebetween, the elongate electrode element being in electrical connection with at least a portion of the elongate passageway; and a resilient member disposed in the gap to prevent direct contact between the elongate electrode element and a wall of the elongate passageway at a location of the gap.

In yet another of its aspects, the present invention relates to a radiation source module comprising the present excimer radiation lamp assembly.

In yet another of its aspects, the present invention relates to a fluid treatment system comprising the present excimer radiation lamp assembly.

In a highly preferred embodiment the present excimer radiation lamp assembly is configured so as to emit ultraviolet radiation.

BRIEF DESCRIPTION OF THE DRAWINGS

Embodiments of the present invention will be described with reference to the accompanying drawings, wherein like reference numerals denote like parts, and in which:

FIG. 4 illustrates a sectional view of a second embodiment of the present excimer radiation source assembly;

FIG. 5 illustrates a sectional view of a third embodiment of the present excimer radiation source assembly;

FIG. 6 illustrates a sectional view of a fourth embodiment of the present excimer radiation source assembly;

FIG. 9 illustrates a sectional view of a sixth embodiment of the present excimer radiation source assembly;

FIG. 10 is an enlarged cross sectional view of a portion of FIG. 9; and

DETAILED DESCRIPTION OF THE PREFERRED EMBODIMENTS

Figure 1:
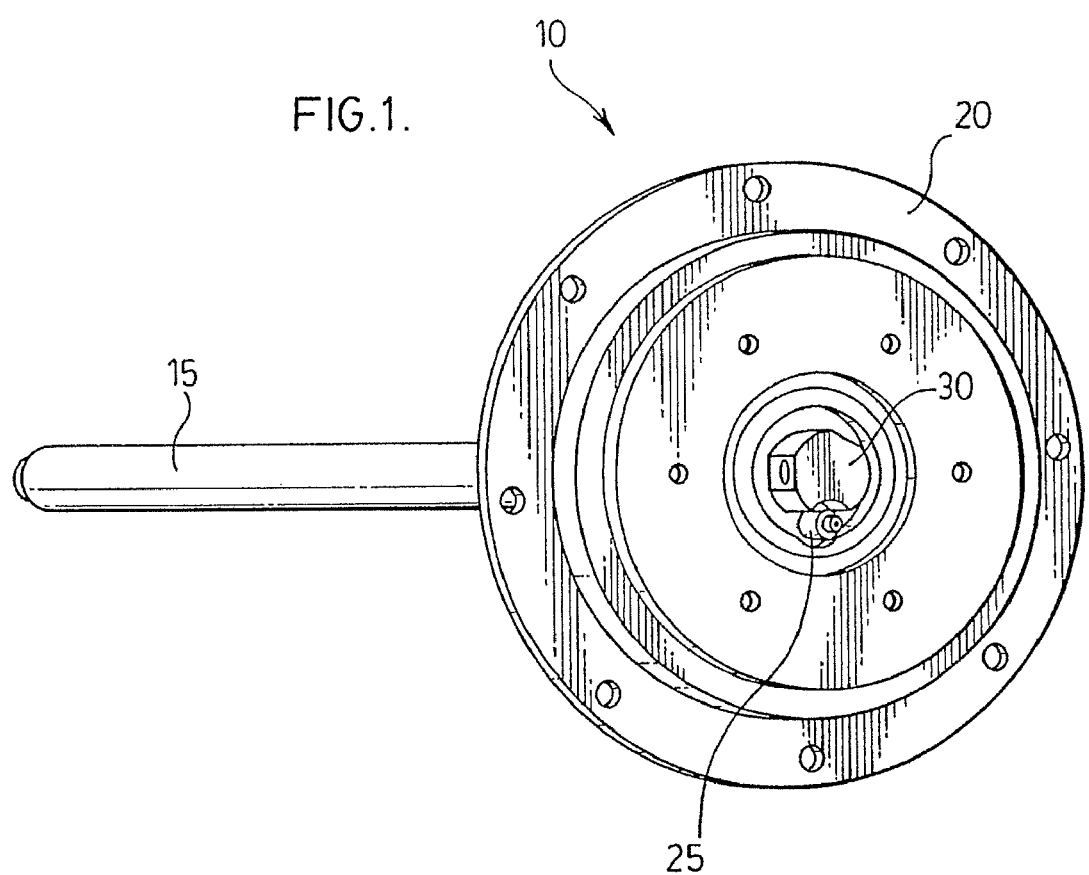
FIG. 1 illustrates a perspective view of the portion of an embodiment of the present excimer radiation lamp assembly.

With reference FIG. 1, there is illustrated an excimer radiation source assembly 10 comprising a center electrode 15 connected to a flanged cover element 20. Disposed in the central portion of flanged cover element 20 is a connector 25 for electrical connection to the so-called hot electrode. Also disposed in the central portion of flanged cover element 20 is a connector 30 for connection to a supply of coolant.

The supply of coolant to connector 30 will be discussed below with reference to preferred embodiments of the present excimer radiation lamp assembly. It will be appreciated by those of skill in the art that excimer radiation source assembly 10 includes an annular radiation emitting element that is not shown for clarity in FIG. 1 but will be shown herein below with reference to preferred embodiments.

Figure 2:
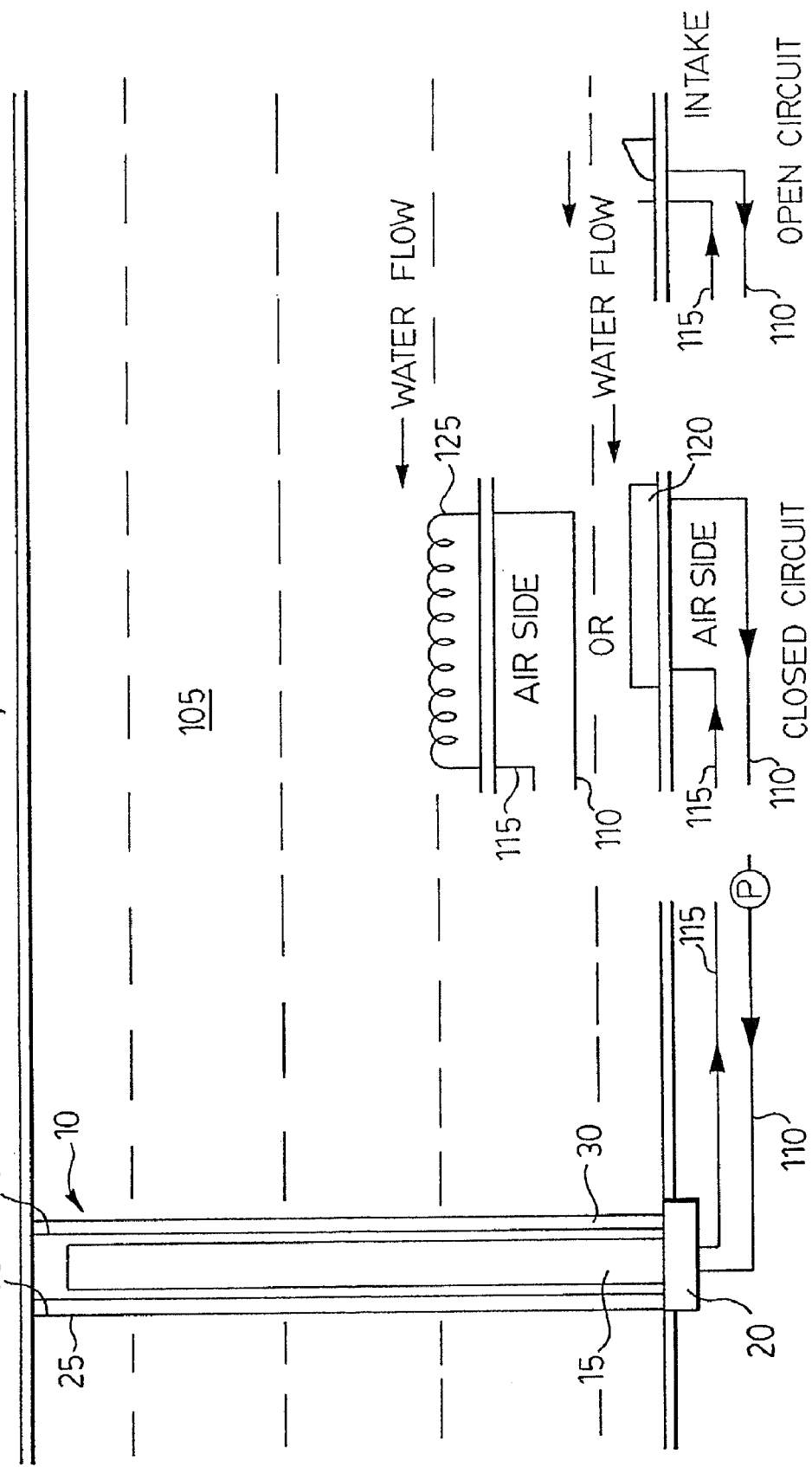
FIG. 2 illustrates a schematic of the use of open and closed circuits for cooling the present excimer radiation lamp assembly.

With reference to FIG. 2, there are illustrated preferred embodiments of implementation of the present excimer radiation lamp assembly.

Specifically, a fluid treatment system 100 is provided and includes a closed fluid treatment zone 105 through which fluid flows as illustrated.

Disposed in fluid treatment zone 105 is a excimer radiation lamp assembly 10. As shown, excimer radiation lamp assembly 10 comprises center electrode 15 and flanged cover element 20. Center electrode 15 is disposed coaxially with respect to an annular radiation emitting element 25 having an annular chamber 30. A phosphor material (not shown) may be applied to one or both, preferably both, of surfaces 35 and 40 of annular chamber 30.

As shown, excimer radiation lamp assembly 10 is connected to a coolant input line 110 and a coolant output line 115.

In FIG. 2, there are illustrated two general approaches to effecting cooling of excimer radiation lamp assembly 10.

First, there is illustrated a so-called closed circuit. In a first embodiment of the closed circuit, coolant output line 115 is passed through a heat exchange element 120 disposed in water passing through fluid treatment zone 105. In a second embodiment, coolant output line 115 is connected to a heat exchange coil 125 disposed in water passing through fluid treatment zone 105. In each of these embodiments, coolant at a relatively high temperature in coolant output line 115 is subjected to heat exchange with relatively cool water passing through fluid treatment zone 105 such that relatively cool coolant is circulated back to excimer radiation lamp assembly 10 via coolant input line 110.

In the open circuit, water is taken from fluid treatment zone 105 and fed to excimer radiation source assembly 10 via coolant input line 110. Spent coolant from excimer radiation lamp assembly 10 is fed into fluid treatment zone 105 by coolant output line 115. This process is repeated in a circuitous manner.

Figure 3:
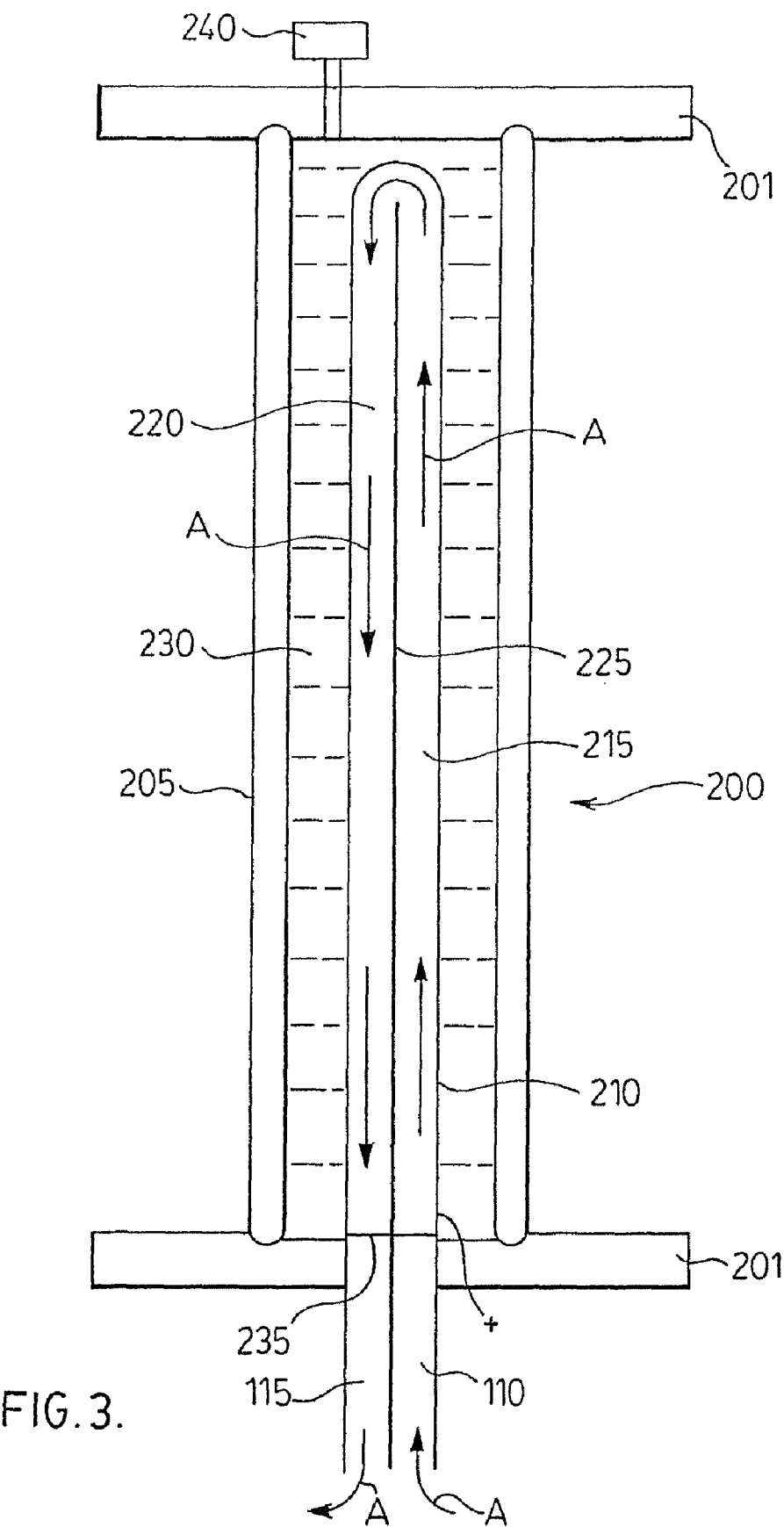
FIG. 3 illustrates a sectional view of a first embodiment of the present excimer radiation source assembly.

With reference to FIG. 3, there is illustrated an excimer radiation lamp assembly 200 disposed between a pair of walls 201 of a fluid treatment system.

Excimer radiation lamp assembly 200 comprises an annular radiation emitting element 205 that is generally similar in construction to radiation emitting element 25 discussed above with reference to FIG. 2.

Disposed coaxially within annular radiation emitting element 205 is a center electrode 210. Center electrode 210 comprises a first passageway 215 and a second passageway 220. First passageway 215 and second passageway 220 are separated by a baffle element 225. Disposed between annular radiation emitting element 205 and center electrode 210 is a conductive or dielectric fluid 230.

Disposed near a proximal portion of center electrode 210 is a electrically isolating element 235. The portion of center electrode 210 located distally of electrically isolating element 235 is connected to a voltage source as shown. Reactor wall 201 near the distal portion of center electrode 210 is connected to a pressure relief valve 240.

Excimer radiation lamp assembly 200 may be used in the following matter. Voltage is applied to center electrode 210. This voltage is applied to radiation emitting element 205 via conductive fluid 230 resulting in emission of radiation, preferably ultraviolet radiation. Concurrent with this is an increase in temperature of excimer radiation lamp assembly 200.

It is important to control the temperature of excimer radiation lamp assembly 200 to optimize the prescribed radiation being emitted therefrom. To achieve this, a non-conductive coolant is passed through first passageway 215 and second passageway 220 in the direction of arrows A. As shown in FIG. 3, the non-conductive coolant is connected to excimer radiation lamp assembly via coolant intake line 110 and coolant output line 115. Lines 110 and 115 can be connected to a closed or open circuit as discussed above with reference to FIG. 2.

With reference to FIG. 4, there is illustrated an excimer radiation lamp assembly 300. In FIG. 4, elements with the same last two digits as those used in FIG. 3, are intended to denote similar structure. The principal modification in FIG. 4 compared with FIG. 3, is the use of a longer cooling circuit within central electrode 310. Specifically, a series electrically insulated flow piping 350 is arranged to provide a series of passageways 315, 320, 317 and 322. These passageways are separated by a series of baffle plates 325, 326 and 327.

Center electrode 310 is connected to a source of electricity (not shown) via a connector 355.

Walls 305 of the fluid treatment system are electrically isolated from excimer radiation lamp assembly 300 via insulating element 360.

Excimer radiation lamp assembly 300 may be operated in a manner similar to that discussed above with reference to FIG. 3. An advantage of this approach is that it permits the use of a partially conductive fluid (e.g., tap water). As the length of the circuit is increase the resistance to current is also increased.

With reference to FIG. 5, there is illustrated an excimer radiation lamp assembly 400. Excimer radiation lamp assembly 400 is attached to a wall 401 of a fluid treatment system.

Excimer radiation lamp assembly 400 comprises an annular radiation emitting element 405 having disposed coaxially therein a center electrode/heat pipe 410. Center electrode/heat pipe 410 is connected to a heat transfer element 412.

Center electrode/heat pipe 410 is connected to a source of electricity (not shown) via an electrical connector 455.

The general operation of heat pipes is known in the art. Thus, a heat pipe operates by transferring heat from an element connected to a distal portion of the heat pipe. The heat transferred to the distal portion of the heat pipe causes evaporation of a fluid (e.g., water, mercury and the like) in an enclosure in the heat pipe to form a vapour. This vapour is then transported to a proximal portion of the heat pipe after which the fluid is condensed to form a liquid in the proximal portion of the heat pipe. During condensation of the liquid, heat is liberated from the proximal portion of the heat pipe. The condensed liquid is then transported back to the distal portion of the heat pipe via a wick or capillary structure in the heat pipe. In some cases, it is possible to eliminate the wick, particularly if the heat pipe is oriented in a substantially vertical manner thereby allowing gravity to facilitate transport of the condensed liquid back to the distal portion of the heat pipe.

The heat pipe includes a container (or enclosure) to isolate the working fluid (and create a partial internal vacuum) from the outside environment. The selection of the container material depends on factors such as: compatibility with the working fluid and external environment, strength to weight ratio, thermal conductivity, ease of fabrication, porosity and the like.

The selection of the working fluid is conventional. The factors involved in selecting the working fluid include: compatibility with wick and enclosure materials, good thermal stability, wettability of wick and enclosure materials, vapour pressure not too high or low over the operating temperature range, high latent heat, high thermal conductivities, low liquid and vapour viscosities, high surface tension, the operating temperature range and acceptable freezing or pour point.

The wick or capillary structure is a porous structure and can be made of a material such as steel, aluminum, nickel or copper. It is also possible to use so-called metal foams and felts. As stated above, in certain cases, the use of a wick or capillary structure is optional.

In the present excimer radiation lamp assembly, a heat pipe may be used advantageously to transport or transfer heat away from the central area of the radiation emitting portion of the lamp assembly to an area remote therefrom. In some embodiments, it is desirable to dissipate the transferred heat from the remote area, for example, by using a reactor wall, air cool fins, active cooling (e.g., water loops around the distal end of the heat pipe) and the like.

With reference to FIG. 6, there is illustrated an excimer radiation lamp assembly 500 which is a modification of excimer radiation lamp assembly 400 shown in FIG. 5. Specifically, in excimer radiation lamp assembly 500, the heat pipe is actually integral with the lamp and there is no gap between the center electrode and annular radiation emitting portion 505. In FIG. 6, the heat pipe is denoted by the reference numeral 506. Also, a distal portion of excimer radiation lamp assembly 500 comprises a vacuum tight element 507.

A proximal portion of excimer radiation lamp assembly 500 comprises a vacuum tight cap and thermal connection element 508.

Excimer radiation lamp assembly 500 may be operated as described above.

Figure 7:
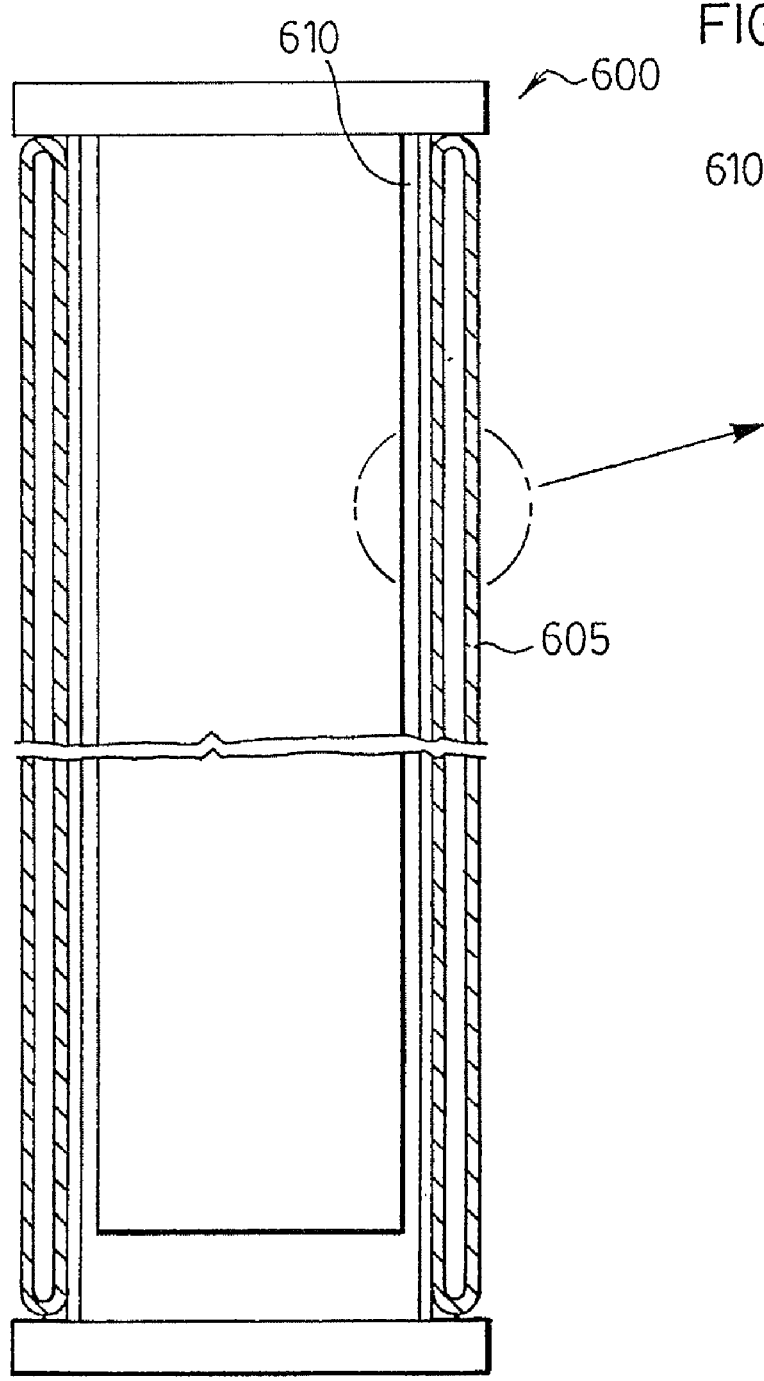
FIG. 7 illustrates a sectional view of a fifth embodiment of the present excimer radiation source assembly.
Figure 8:
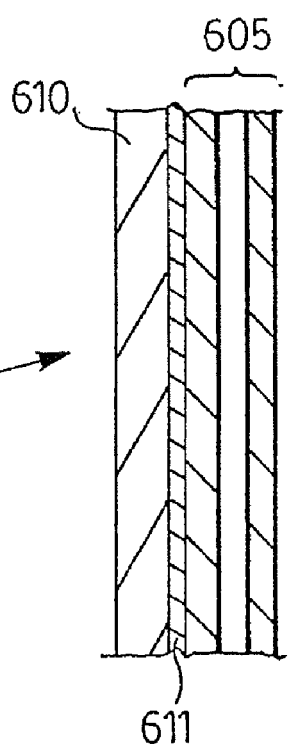
FIG. 8 is an enlarged sectional view of a portion of the embodiment illustrated in FIG. 7.

With reference to FIG. 7, there is illustrated an excimer radiation lamp assembly 600 comprising a center electrode 610 disposed coaxially within an annular radiation emitting portion 605. As shown in FIG. 8, a compressible material 611 is disposed between the surfaces of center electrode 610 and the inner surface of annular radiation emitting portion 605. The provision of compressible material 611 compensates for expansion/contraction of center electrode and/or annular radiation emitting portion 605 as excimer radiation lamp assembly 600 is heated.

The precise nature of compressible material 611 is not particularly restricted. Physically, compressible material 611 may be a gel, a foam element or a fluid.

With reference to FIGS. 9 and 10, there is illustrated an excimer radiation lamp assembly 700 comprising an annular radiation emitting portion 705 having disposed coaxially therein a center electrode 710.

Excimer radiation lamp assembly 700 is disposed between a pair of flanges 712. An O-ring 713 (or similar sealing element) is disposed between flanged 712 and annular radiation emitting portion 705.

A constant load spring 714 is disposed on an opposed surface of flanged 712 at one end of excimer radiation lamp assembly 700.

Constant load spring 714 is used as part of a clamping device for compression of excimer radiation lamp assembly 710 to increase lamp strength under bending stresses, particularly when excimer radiation lamp assembly 700 is disposed in a flow of fluid with significant hydraulic head.

Figure 11:
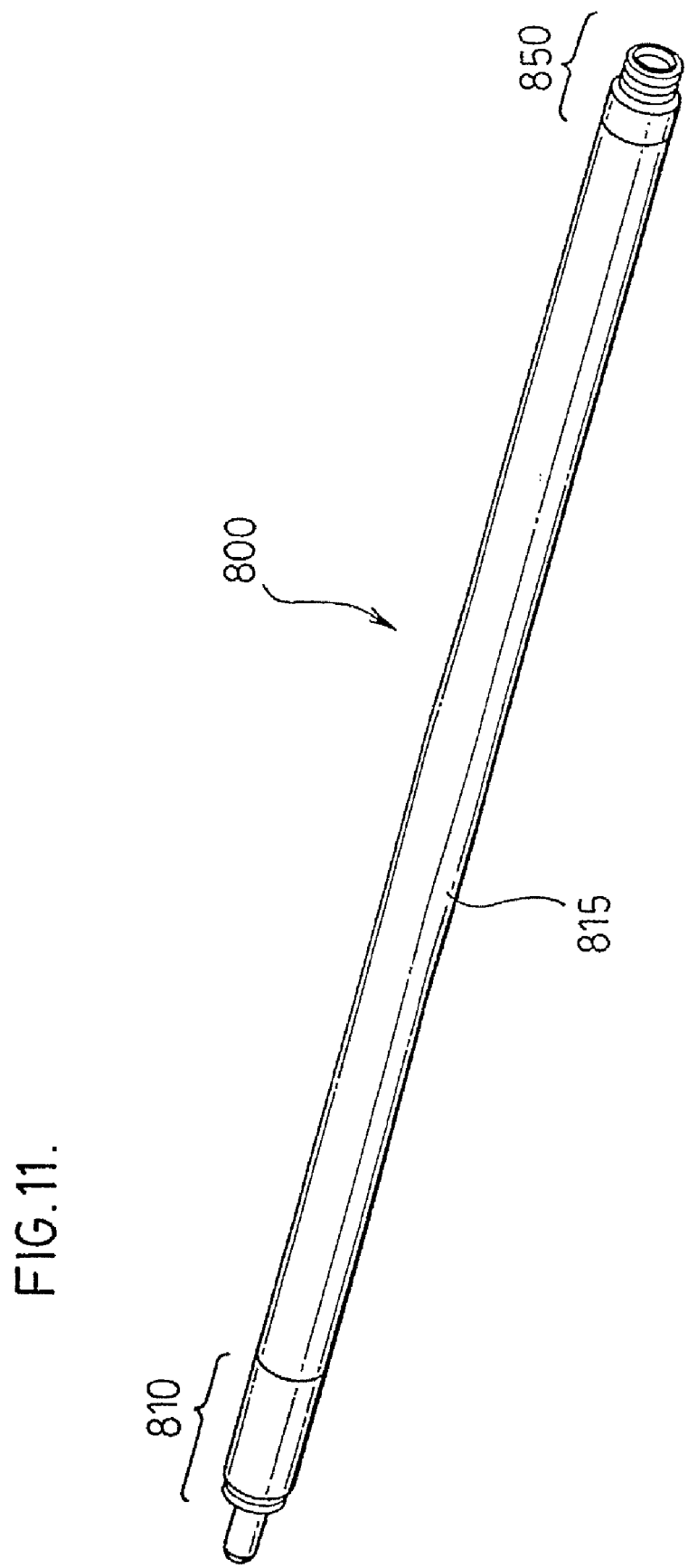
FIGS. 11-13 illustrates various views of a seventh embodiment of the present excimer radiation source assembly.
Figure 12:
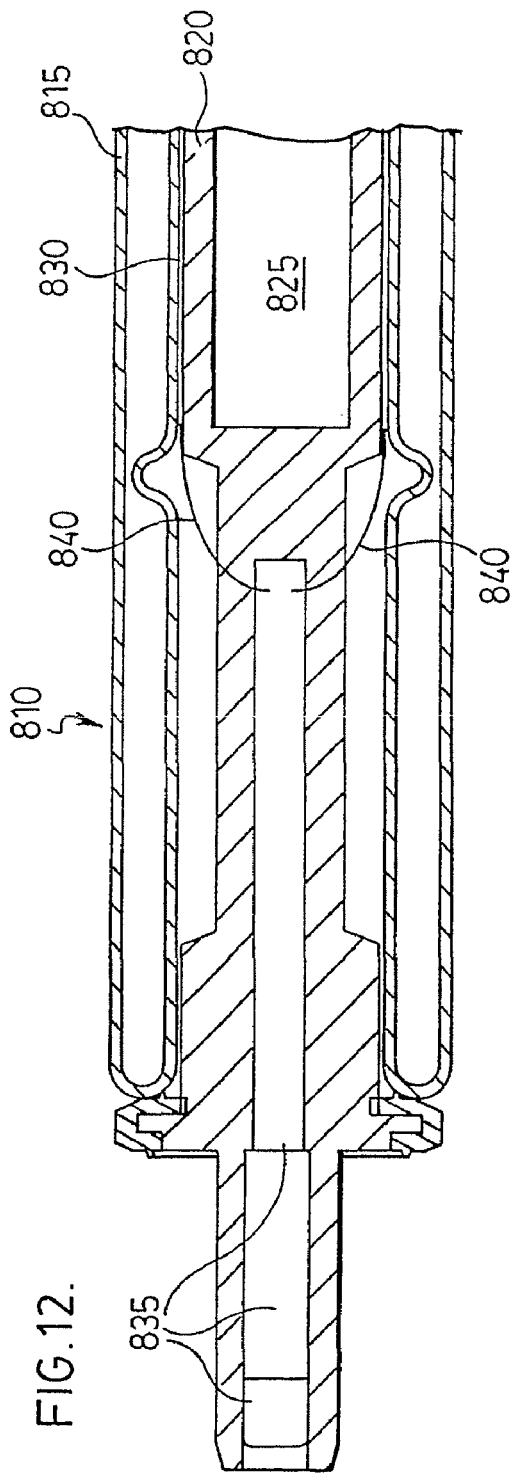
Figure 13:
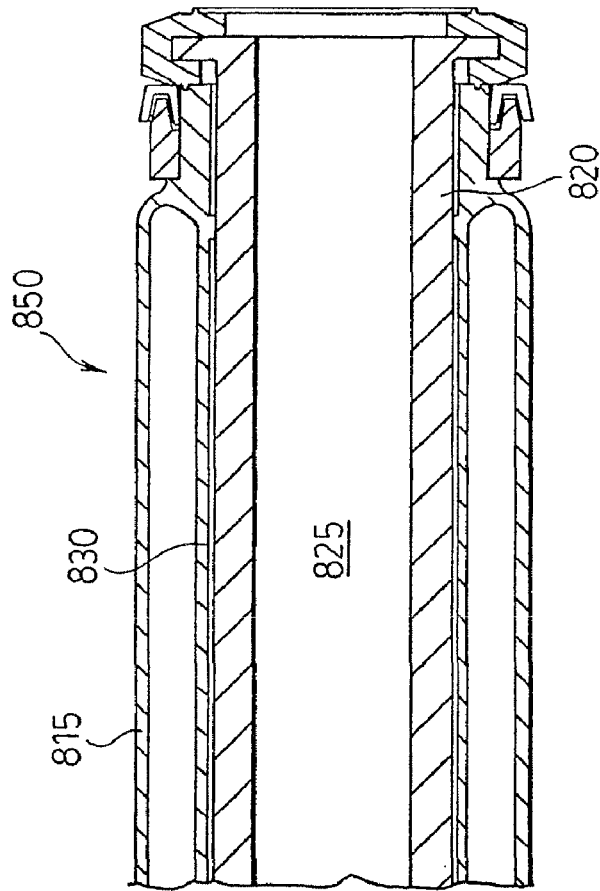

With reference to FIGS. 11-13, there is illustrated an excimer radiation lamp assembly 800 having a first end 810 and a second end 850. An annular radiation emitting portion 815 is disposed between first end 810 and second end 850.

With particular reference to FIGS. 12 and 13, first end 810 and second end 850 comprise a dielectric barrier element 820 which extends along the interior of annular radiation emitting portion 815. A cooling passageway 825 is provided in dielectric barrier element 820 for receiving a cooling element (not shown for clarity) such as those described above—e.g., a cooling circuit, a heat pipe and the like.

An electrode element 830 is disposed between annular radiation emitting portion 815 and dielectric barrier element 820. Electrode element 830 is connecting to an electrical connector 830 by a pair of electrical leads 840.

Preferably dielectric barrier element 820 is an electrical isolation element that serves to separate the high voltage of the hot electrode from the cooling element. This allows the cooling element to be grounded, which greatly increases the safety of and simplifies the design of the cooling system. This is a significant improvement over the known designs, which typically have a high voltage potential on the cooling element.

Dielectric barrier element 820 preferably is configured to have appropriate electrical properties to minimize losses from (high voltage) electrode 830 to the grounded cooling element. Such configuration of dielectric barrier element 820 is within the purview of a person skilled in art.

Dielectric barrier element 820 preferably is also configured to have appropriate thermal properties in order to promote good heat transfer from the annular radiation emitting portion 815 and electrode 830 to the cooling element (not shown for clarity). Such configuration of dielectric barrier element 820 is within the purview of a person skilled in art.

All publications, patents and patent applications referred to herein are incorporated by reference in their entirety to the same extent as if each individual publication, patent or patent application was specifically and individually indicated to be incorporated by reference in its entirety. For greater, two copending U.S. provisional patent applications 60/752,024 (Gowlings Ref: T8469433US) and 60/752,026 (Gowlings Ref: T8469434US), both filed on Dec. 21, 2005 in the names of the present inventors, are each incorporated herein by reference.

What is claimed is:

1. An excimer radiation lamp assembly comprising:
   an elongate member having an annular cross-section to define an elongate passageway aligned with a longitudinal axis of the lamp assembly;
   an electrode element in electrical connection with at least a portion of the elongate passageway;
   a cooling element disposed in the elongate passageway, the cooling element being electrically isolated with respect to the electrode element; and
   an electrically isolating element disposed interiorly of the electrode element.

2. The excimer radiation lamp assembly defined in claim 1, wherein the electrically isolating element is selected from the group consisting of elastomers, polymers, ceramics and mixtures thereof.

3. The excimer radiation lamp assembly defined in claim 1, wherein the electrically isolating element is a fluid.

4. The excimer radiation lamp assembly defined in claim 1, wherein the electrically isolating element is a gel.

5. The excimer radiation lamp assembly defined in claim 1, wherein the cooling element comprises a first passageway and a second passageway, each of the first passageway and the second passageway being configured to receive a coolant.

6. The excimer radiation lamp assembly defined in claim 5, wherein the first passageway and the second passageway are configured to receive a liquid coolant.

7. The excimer radiation lamp assembly defined in claim 5, wherein the first passageway and the second passageway are interconnected.

8. The excimer radiation lamp assembly defined in claim 5, wherein the first passageway and the second passageway are configured such that the direction of coolant flow in the first passageway is substantially opposite to the direction of coolant flow in the second passageway.

9. The excimer radiation lamp assembly defined in claim 1, wherein the cooling element comprises a closed circuit.

10. The excimer radiation lamp assembly defined in claim 9, wherein the closed circuit is in heat exchange contact with a fluid being radiated by the excimer radiation lamp assembly.

11. The excimer radiation lamp assembly defined in claim 9, wherein the closed circuit is in heat exchange contact with a cooling fluid.

12. The excimer radiation lamp assembly defined in claim 1, wherein the cooling element comprises an open circuit.

13. The excimer radiation lamp assembly defined in claim 12, wherein the open circuit is in fluid communication with a fluid being radiated by the excimer radiation lamp assembly.

14. An excimer radiation lamp assembly comprising:
   an elongate member having an annular cross-section to define an elongate passageway aligned with a longitudinal axis of the lamp assembly;
   an electrode element in electrical connection with at least a portion of the elongate passageway; and
   a cooling circuit disposed in the elongate passageway and configured to receive a coolant, the cooling circuit having: (i) a coolant inlet, (ii) a coolant outlet and (iii) a length such that an applied voltage at the electrical connection is reduced by a factor of at least 0.10 at the coolant inlet.

15. An excimer radiation lamp assembly comprising:
   an elongate member having an annular cross-section to define an elongate passageway aligned with a longitudinal axis of the lamp assembly;
   an electrode element in electrical connection with at least a portion of the elongate passageway; and
   a cooling circuit disposed in the elongate passageway and configured to receive a coolant, the cooling circuit having: (i) a coolant inlet, (ii) a coolant outlet and (iii) a cooling loop configured to be in heat exchange contact with fluid from a fluid treatment system in which the radiation assembly is disposed.

16. An excimer radiation lamp assembly comprising:
   an elongate member having an annular cross-section to define an elongate passageway aligned with a longitudinal axis of the lamp assembly;
   an electrode element in electrical connection with at least a portion of the elongate passageway; and
   a cooling circuit disposed in the elongate passageway and configured to receive a coolant, the cooling circuit having: (i) a coolant inlet in fluid communication with fluid from a fluid treatment system in which the radiation assembly is disposed, (ii) a coolant outlet in fluid communication with fluid from a fluid treatment system in which the radiation assembly is disposed and (iii) motive means to cycle the coolant from the cooling circuit to the fluid treatment system.

17. An excimer radiation lamp assembly comprising:
   an elongate member having an annular cross-section to define an elongate passageway aligned with a longitudinal axis of the lamp assembly;

an elongate electrode element disposed in the elongate passageway to define an annular passageway configured to receive an electrically conductive fluid; and a cooling element disposed in the elongate electrode, the cooling element comprising a substantially electrically non-conductive heat transfer element configured to convey heat from the elongate electrode.

18. An excimer radiation lamp assembly comprising:

an elongate member having an annular cross-section to define an elongate passageway aligned with a longitudinal axis of the lamp assembly;

an electrode element in electrical connection with at least a portion of the elongate passageway; and the elongate passageway comprising a heat pipe element, the heat pipe element configured to transfer heat from the electrode element.

19. An excimer radiation lamp assembly comprising:

an elongate member having an annular cross-section to define an elongate passageway aligned with a longitudinal axis of the lamp assembly;

an elongate electrode element disposed in the elongate passageway to define a gap therebetween, the elongate electrode element being in electrical connection with at least a portion of the elongate passageway; and a resilient member disposed in the gap to prevent direct contact between the elongate electrode element and a wall of the elongate passageway at a location of the gap.

* * * * *